(12) United States Patent
Christie et al.

(10) Patent No.: US 9,220,913 B2
(45) Date of Patent: Dec. 29, 2015

(54) MULTI-MODE IMPLANTABLE MEDICAL DEVICE

(71) Applicant: Medtronic, Inc., Minneapolis, MN (US)

(72) Inventors: Melissa G. T. Christie, Andover, MN (US); Amy E. Thompson-Nauman, Ham Lake, MN (US); Becky L. Dolan, Chisago, MN (US); Paul J. DeGroot, Shoreview, MN (US); Rick D. McVenes, Isanti, MN (US)

(73) Assignee: Medtronics, Inc., Minneapolis, MN (US)

( * ) Notice: Subject to any disclaimer, the term of this patent is extended or adjusted under 35 U.S.C. 154(b) by 8 days.

(21) Appl. No.: 14/270,804

(22) Filed: May 6, 2014

(65) Prior Publication Data
US 2014/0330328 A1  Nov. 6, 2014

Related U.S. Application Data

(60) Provisional application No. 61/819,926, filed on May 6, 2013.

(51) Int. Cl.
| | | |
|---|---|---|
| *A61N 1/372* | (2006.01) | |
| *A61N 1/39* | (2006.01) | |
| *A61N 1/375* | (2006.01) | |

(Continued)

(52) U.S. Cl.
CPC ............ *A61N 1/3962* (2013.01); *A61N 1/3688* (2013.01); *A61N 1/3752* (2013.01); *A61N 1/3925* (2013.01); *A61N 1/0504* (2013.01); *A61N 1/0563* (2013.01); *A61N 2001/083* (2013.01)

(58) Field of Classification Search
CPC ... A61N 1/3686; A61N 1/375; A61N 1/3752; A61N 1/3912; A61N 1/3962; A61N 1/3968
USPC .................................. 607/4, 7, 36, 38, 62, 63
See application file for complete search history.

(56) References Cited

U.S. PATENT DOCUMENTS

| | | |
|---|---|---|
| 4,030,509 A | 6/1977 | Heilman et al. |
| 4,146,037 A | 3/1979 | Flynn et al. |

(Continued)

FOREIGN PATENT DOCUMENTS

| | | |
|---|---|---|
| WO | 0123035 A1 | 4/2001 |
| WO | 2004073506 A2 | 9/2004 |
| WO | 2010047893 A1 | 4/2010 |

OTHER PUBLICATIONS

Ganapathy et al., "Implantable Device to Monitor Cardiac Activity with Sternal Wires," Pace, vol. 37, Dec. 2014, 11 pages.

(Continued)

*Primary Examiner* — Allen Porter, Jr.
(74) *Attorney, Agent, or Firm* — Evans M. Mburu; Stephen W. Bauer; Michael J. Ostrom

(57) ABSTRACT

Techniques and methods for determining the number and type of leads that are connected to an implantable medical device (IMD) system are disclosed. The IMD system is configured having at least two modes of operation, the modes of operation corresponding to the number and type of leads that are coupled to the IMD system. In accordance with aspects of the disclosure, one of the at least two modes may be selected based on the determination of the number and type of leads that are connected to the IMD system.

26 Claims, 6 Drawing Sheets

(51) Int. Cl.
    *A61N 1/368* (2006.01)
    *A61N 1/08* (2006.01)
    *A61N 1/05* (2006.01)

(56) References Cited

U.S. PATENT DOCUMENTS

| | | |
|---|---|---|
| 4,270,549 A | 6/1981 | Heilman |
| 4,280,510 A | 7/1981 | O'Neill |
| 4,291,707 A | 9/1981 | Heilman et al. |
| 4,437,475 A | 3/1984 | White |
| 4,512,351 A | 4/1985 | Pohndorf |
| 4,538,624 A | 9/1985 | Tarjan |
| 4,765,341 A | 8/1988 | Mower et al. |
| 4,832,687 A | 5/1989 | Smith, III |
| 5,036,854 A | 8/1991 | Schollmeyer et al. |
| 5,125,904 A | 6/1992 | Lee |
| 5,176,135 A | 1/1993 | Fain et al. |
| 5,255,691 A | 10/1993 | Otten |
| 5,255,692 A | 10/1993 | Neubauer et al. |
| 5,300,106 A | 4/1994 | Dahl et al. |
| 5,312,355 A | 5/1994 | Lee |
| 5,441,504 A | 8/1995 | Pohndorf et al. |
| 5,456,699 A | 10/1995 | Armstrong |
| 5,509,924 A | 4/1996 | Paspa et al. |
| 5,534,018 A | 7/1996 | Wahlstrand et al. |
| 5,613,953 A | 3/1997 | Pohndorf |
| 5,690,648 A | 11/1997 | Fogarty et al. |
| 5,944,732 A | 8/1999 | Raulerson et al. |
| 5,951,518 A | 9/1999 | Licata et al. |
| 6,032,079 A | 2/2000 | KenKnight et al. |
| 6,104,957 A | 8/2000 | Alo et al. |
| 6,122,552 A | 9/2000 | Tockman et al. |
| 6,159,198 A | 12/2000 | Gardeski et al. |
| 6,228,052 B1 | 5/2001 | Pohndorf |
| 6,324,414 B1 | 11/2001 | Gibbons et al. |
| 6,415,187 B1 | 7/2002 | Kuzma et al. |
| 6,445,954 B1 | 9/2002 | Olive et al. |
| 6,544,247 B1 | 4/2003 | Gardeski et al. |
| 6,721,597 B1 | 4/2004 | Bardy et al. |
| 6,730,083 B2 | 5/2004 | Freigang et al. |
| 6,733,500 B2 | 5/2004 | Kelley et al. |
| 6,749,574 B2 | 6/2004 | O'Keefe |
| 6,770,070 B1 | 8/2004 | Balbierz |
| 6,772,014 B2 | 8/2004 | Coe et al. |
| 6,836,687 B2 | 12/2004 | Kelley et al. |
| 6,868,291 B1 | 3/2005 | Bonner et al. |
| 6,887,229 B1 | 5/2005 | Kurth |
| 7,033,326 B1 | 4/2006 | Pianca et al. |
| 7,050,851 B2 | 5/2006 | Plombon et al. |
| 7,069,083 B2 | 6/2006 | Finch et al. |
| 7,117,039 B2 | 10/2006 | Manning et al. |
| 7,195,637 B2 | 3/2007 | Mika |
| 7,218,970 B2 | 5/2007 | Ley et al. |
| 7,229,450 B1 | 6/2007 | Chitre et al. |
| 7,288,096 B2 | 10/2007 | Chin |
| 7,316,667 B2 | 1/2008 | Lindstrom et al. |
| 7,322,960 B2 | 1/2008 | Yamamoto et al. |
| 7,369,899 B2 | 5/2008 | Malinowski et al. |
| 7,389,134 B1 | 6/2008 | Karicherla et al. |
| 7,450,997 B1 | 11/2008 | Pianca et al. |
| 7,499,758 B2 | 3/2009 | Cates et al. |
| 7,539,542 B1 | 5/2009 | Malinowski |
| 7,627,375 B2 | 12/2009 | Bardy et al. |
| 7,655,014 B2 | 2/2010 | Ko et al. |
| 7,736,330 B2 | 6/2010 | Bardy |
| 7,761,150 B2 | 7/2010 | Ghanem et al. |
| 7,765,014 B2 | 7/2010 | Eversull et al. |
| 7,837,671 B2 | 11/2010 | Eversull et al. |
| 7,846,088 B2 | 12/2010 | Ness |
| 7,930,028 B2 | 4/2011 | Lang et al. |
| 7,930,040 B1 | 4/2011 | Kelsch et al. |
| 7,983,765 B1 | 7/2011 | Doan et al. |
| 8,060,207 B2 | 11/2011 | Wallace et al. |
| 8,065,020 B2 | 11/2011 | Ley et al. |
| 8,066,702 B2 | 11/2011 | Rittman, III et al. |
| 8,090,451 B2 | 1/2012 | Tyson, Jr. |
| 8,155,755 B2 | 4/2012 | Flynn et al. |
| 8,157,813 B2 | 4/2012 | Ko et al. |
| 8,260,436 B2 | 9/2012 | Gerber et al. |
| 8,280,527 B2 | 10/2012 | Eckerdal et al. |
| 8,340,779 B2 | 12/2012 | Harris et al. |
| 8,355,786 B2 | 1/2013 | Malinowski |
| 8,386,052 B2 | 2/2013 | Harris et al. |
| 8,435,208 B2 | 5/2013 | Bardy |
| 8,442,620 B2 | 5/2013 | Silipo et al. |
| 8,452,421 B2 | 5/2013 | Thenuwara et al. |
| 8,478,424 B2 | 7/2013 | Tronnes |
| 8,478,426 B2 | 7/2013 | Barker |
| 8,731,679 B2 * | 5/2014 | Ternes et al. ............ 607/59 |
| 8,886,311 B2 | 11/2014 | Anderson et al. |
| 2002/0120294 A1 | 8/2002 | Kroll |
| 2003/0088278 A1 | 5/2003 | Bardy et al. |
| 2003/0114908 A1 | 6/2003 | Flach |
| 2004/0059348 A1 | 3/2004 | Geske et al. |
| 2004/0102829 A1 | 5/2004 | Bonner et al. |
| 2004/0210293 A1 | 10/2004 | Bardy et al. |
| 2004/0215240 A1 | 10/2004 | Lovett et al. |
| 2004/0230229 A1 * | 11/2004 | Lovett et al. ............. 607/4 |
| 2004/0236396 A1 | 11/2004 | Coe et al. |
| 2005/0004615 A1 * | 1/2005 | Sanders ............. 607/36 |
| 2005/0049663 A1 | 3/2005 | Harris et al. |
| 2005/0131505 A1 | 6/2005 | Yokoyama |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0253181 A1 | 11/2006 | Schulman et al. |
| 2007/0100409 A1 | 5/2007 | Worley et al. |
| 2007/0208402 A1 | 9/2007 | Helland et al. |
| 2007/0249992 A1 | 10/2007 | Bardy |
| 2008/0046056 A1 | 2/2008 | O'Connor |
| 2008/0243219 A1 | 10/2008 | Malinowski et al. |
| 2008/0269716 A1 | 10/2008 | Bonde et al. |
| 2009/0157091 A1 | 6/2009 | Buysman |
| 2009/0222021 A1 | 9/2009 | Chang |
| 2009/0259283 A1 | 10/2009 | Brandt et al. |
| 2009/0264780 A1 | 10/2009 | Schilling |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0217298 A1 | 8/2010 | Bardy |
| 2010/0217301 A1 | 8/2010 | Bardy |
| 2010/0249696 A1 | 9/2010 | Bardy |
| 2010/0305428 A1 | 12/2010 | Bonner et al. |
| 2010/0318098 A1 | 12/2010 | Lund et al. |
| 2011/0009933 A1 | 1/2011 | Barker |
| 2011/0224680 A1 | 9/2011 | Barker |
| 2011/0224681 A1 | 9/2011 | McDonald |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0123496 A1 * | 5/2012 | Schotzko et al. ........... 607/28 |
| 2012/0191106 A1 | 7/2012 | Ko et al. |
| 2012/0209283 A1 | 8/2012 | Zhu |
| 2012/0209285 A1 | 8/2012 | Barker et al. |
| 2013/0103049 A1 | 4/2013 | Bonde |
| 2013/0158564 A1 | 6/2013 | Harris et al. |
| 2013/0238067 A1 | 9/2013 | Baudino |

OTHER PUBLICATIONS

Guenther et al., "Substernal Lead Implantation: A Novel Option to Manage DFT Failure in S-ICD patients," Clinical Research Cardiology, Published On-line Oct. 2, 2014, 3 pages.

(56) References Cited

OTHER PUBLICATIONS

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.
Obadia, et al., "New Approach for Implantation of Automatic Defibrillators Using Videothoracoscopy", Journal Ann Cardiol Angeiol (Paris); Sep. 1994; 43 (7) Abstract Only, 1 page.
Lemmer, "Defibrillator Patch Constriction, Letter to the Editor", The Annals of Thoracic Surgery, 1996, 1 page.
Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.
Damiano, "Implantation of Cardioverter Defibrillators in the Post-Sternotomy Patient", The Annals of Thoracic Surgery, 1992; 53: pp. 978-983.
Piccione, et al., "Erosion of Extrapericardial Implantable Cardioverter Defibrillator Patch Through the Gastic Fundus with Fistulous Tract Information", Cardiology in Review; 2006; 14, e21-e23 pages.
Vyhmeister et al., "Simple Approach for Extrapericardial Placement of Defibrillator Patches via Median Sternotomy", The Annals of Thoracic Surgery; 1994; 57: 4 pages.
Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.
Obadia et al., "Thoracoscopic Approach to Implantable Cardioverter Defibrillator Patch Electrode Implantation", Pacing and Clinical Electrophysiology; Jun. 1996; vol. 19; 6 pages.
Shapira, et al., A Simplied Method for Implantation of Automatic Cardioverter Defibrillator in Patients with Previous Cardiac Surgery, Pacing and Clinical Electrophysiology, Jan. Part I, 1993, vol. 16; 6 pages.
Quigley et al., "Migration of an Automatic Implantable Cardioverter-Defibrillator Patch Causing Massive Hemothorax", Journal Texas Heart Institute, Nov. 1, 1996; vol. 23, 4 pages.
Karwande et al., Bilateral Anterior Thoracotomy for Automatic Implantable Cardioverter Defibrillator Placement in Patients with Previous Sternotomy, The Annals of Thoracic Surgery; Oct. 1992; 54(4); 3 pages.

Bielefeld et al., "Thoracoscopic Placement of Implantable Cardioverter-Defibrillator Patch Leads in Sheep", Circulation; Nov. 1993, vol. 88, No. 5, Part 2; 5 pages.
Frame et al., "Long-Term Stability of Defibrillation Thresholds with Intrapericardial Defibrillator Patches", Pacing and Clinical Electrophysiology, Jan. 1993, Part II, vol. 16, 6 pages.
Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.
Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.
Bolling et al., "Automatic Internal Cardioverter Defibrillator: A Bridge to Heart Transplantation", Heart Lung Transplantation, Abstract Only, Jul.-Aug. 1991, 1 page.
Steinke et al., Subepicardial Infarction, Myocardial Impression, and Ventricular Penetration by Sutureless Electrode and Leads, Chest; 70: Jul. 1, 1976, 2 pages.
Avogadros Lab Supply Inc., Catalog; Scoopula with Beech Wood Handle, can be found on-line at http://www.avogadro-lab-supply.com/search.php, accessed Oct. 6, 2013, 1 page.
Cigna et al., A New Technique for Substernal Colon Transposition with a Breast Dissector: Report of 39 Cases, Journal of Plastic, Reconstructive and Aesthetic Surgery, 2006:59, 4 pages.
Tung et al., "Minimal Invasive Extra Cardiac Placement of High Voltage Defibrillator Leads", Poster 3; S200 Abstract, PO-3-4; St. Paul Hospital, Vancouver, British Columbia, Canada, 1 page.
Molina et al, "An Epicardial Subxiphoid Implantable Defibrillator Lead: Superior Effectiveness After Failure of Stndard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.
Baudoin et al., The Superior Epigastric Artery Does Not Pass Through Larrey's Space (Trigonum Sternocostale) Surgical Radiol Anat (2003), 25: 259-262.
Haydin et al., "Subxiphoid Approach to Epicardial Implantation of Implantable Cardioverter Defibrillators in Children", PACE, vol. 36, Aug. 2013, 5 pages.

* cited by examiner

MULTI-MODE IMPLANTABLE MEDICAL DEVICE

CROSS-REFERENCE TO RELATED APPLICATIONS

This application claims the benefit of priority from U.S. Provisional Application No. 61/819,926, filed on May 6, 2013, the content of which is incorporated herein by reference in its entirety.

FIELD

The present disclosure relates to implantable medical devices. More particularly, this disclosure pertains to implantable medical devices that are connected to one or more electrical leads.

BACKGROUND

A wide variety of implanted medical devices (IMDs) for delivering a therapy or monitoring a physiologic condition which can employ one or more elongated implantable medical electrical leads and/or sensors are available. Such IMDs can monitor or deliver therapy to the heart, muscle, nerve, brain, and stomach or other organs. Examples of such IMDs include implantable cardioverter defibrillator devices, which have a pulse generator and one or more electrical leads with one or more electrodes that conduct signals to and receive signals from the patient's heart. More recently, subcutaneous IMDs have been devised to deliver shocks to the heart by the use of a defibrillation lead placed subcutaneously on the torso.

These electrical leads and their electrodes are placed in or proximate to the organ such that an electrical signal between electrodes is capable of stimulating the organ. The electrodes may be configured either to deliver a stimulus to the organ, or to detect or sense an intrinsic electrical event associated with the organ. A programming device or programmer communicates with the medical device through a communication link. One example of a communication link is a telemetry link that provides means for commands and data to be non-invasively transmitted and received between the programmer and the device.

The electrical leads associated with IMDs typically include a lead body extending between a proximal lead end and a distal lead end and incorporate one or more exposed electrode or sensor elements located at or near the distal lead end. One or more elongated electrical conductors extend through the lead body from a connector assembly provided at a proximal lead end for connection with an associated IMD to an electrode located at the distal lead end or along a section of the lead body. Each electrical conductor is typically electrically isolated from other electrical conductors and is encased within an outer sheath insulator, which electrically insulates the lead conductors from body tissue and fluids. The leads can extend from a subcutaneous implantation site of the IMD through an internal body pathway to a desired tissue site. The leads are generally preferred having small diameter, highly flexible, reliable lead bodies that withstand degradation by body fluids and body movements that apply stress and strain to the lead body and the connections made to electrodes.

However, the conventional subcutaneous IMDs are incapable of delivering pacing therapies, such as anti-tachycardia pacing (ATP), without extreme discomfort to the patient. As such, the conventional subcutaneous IMDs are devised to deliver shocks to the heart by the use of a defibrillation lead placed subcutaneously on the torso. There remains a need in the art for improvements to the subcutaneous IMDs to provide a wide range of therapy delivery and sensing options.

SUMMARY

In general, the disclosure relates to implantable medical device (IMD) systems and methods for providing multiple therapies, such as pacing and defibrillation. The IMDs include a device housing assembly and one or more electrical leads. Each lead includes one or more electrodes that discharge electrical current to a target patient site. The variety of lead/electrode combinations allows for a wide range of treatment options directed specifically to a patient's particular cardiac condition. This variety also requires that the medical device be configured to accommodate each specific lead/electrode combination. Therefore, embodiments of the present invention disclose techniques for identifying the lead/electrode combinations associated with a medical device and configuring the functionality of the IMD.

In one aspect, an implantable cardioverter defibrillator (ICD) is provided having at least two ports, each of which is configured to receive a medical electrical lead. For example, an embodiment of the disclosure may include an ICD having two ports. The ICD may be implanted with only one lead connected to one of the two ports. A second lead may be implanted at a later time, subsequent to the implantation, during which time the second lead is then connected to the ICD. Accordingly, the ICD may be configured for a single lead mode of operation, or a multiple lead (multi-lead) mode of operation based on whether a single lead is connected to the ICD, or whether two or more leads are connected to the ICD, respectively.

In other aspects of the disclosure, the ICD is configured to identify the number and type of connected leads. In response to determining the number and type of leads, the ICD is configured to utilize the available leads for performing one or more functions. The functions of the ICD include therapy delivery and sensing. When a given lead is not detected, the ICD may disable the various functions that require the electrodes associated with the lead. In response to detecting the connection of the lead, the ICD enables the functions associated with the lead.

In accordance with other aspects, the disclosure provides an ICD having multiple ports for connection of electrical leads. In some embodiments, each of the ports is associated with a switch that is controllable to facilitate detection of a connected lead. For example, each of the ports includes a switch that is configured to be actuated by a lead in response to insertion of the lead into the port. In other embodiments, the disclosure provides techniques for measurement of an electrical parameter to determine whether a lead is implanted in a given one of the ports.

In one embodiment, the ICD includes a defibrillation lead port and a pacing lead port. A defibrillation lead may be coupled to the defibrillation lead port and a pacing lead may be coupled to the pacing lead port. The ICD may be configured to recognize whether one or both the pacing lead and/or the defibrillation lead is coupled to the pacing lead port and the defibrillation lead port, respectively. In response to the recognition, the ICD assumes or selects either the single lead mode or multi-lead mode based on whether the pacing lead, or the defibrillation lead, or both, is/are coupled to the lead ports. Alternatively, the ICD may be programmable to switch between the single lead mode and the multi-lead mode. The ICD system includes a controller receiving input from the defibrillation lead, pacing lead and/or the ICD to control the pacing pulses and the defibrillation shocks.

In one embodiment of a method of use, a processor automatically determines whether a pacing lead is connected to a pacing lead port of an ICD having a pacing lead port, and whether a defibrillation lead is coupled to the defibrillation lead port. Based on the task of automatically determining, the operating mode of the ICD is selected as one of: (a) a single lead mode in which the ICD is configured to operate without the pacing lead coupled to the pacing lead port, and to provide defibrillation shocks to the patient via the defibrillation lead; (b) a single lead mode in which the ICD is configured to operate with the pacing lead coupled to the pacing lead port, and to provide pacing pulses to a heart of the patient via the pacing lead; and (c) a multi-lead mode in which the ICD is configured to operate with the pacing lead coupled to the pacing lead port, and to provide pacing pulses to a heart of the patient via the pacing lead and provide defibrillation shocks to the patient via the defibrillation lead.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The foregoing and other features of the present invention will be best appreciated with reference to the following detailed description of a specific embodiment of the invention, when read in conjunction with the accompanying drawings, wherein.

DETAILED DESCRIPTION

The following detailed description is illustrative in nature and is not intended to limit the embodiments of the disclosure or the application and uses of such embodiments. Furthermore, there is no intention to be bound by any expressed or implied theory presented in the preceding technical field, background, brief summary or the following detailed description.

The embodiments of the invention are disclosed in the context of an implantable medical device (IMD) system that include, for example, an implantable cardioverter defibrillator (ICD) which may have one or more implantable medical electrical leads coupled thereto. The IMD system may be implantable subcutaneously within a patient and the leads may provide one or more functions such as pacing, defibrillation, and sensing. In the present disclosure, the IMD system is operable in a plurality of modes, with the specific operating mode being selected based on a determination of the leads that are connected to the IMD.

Figure 1A:
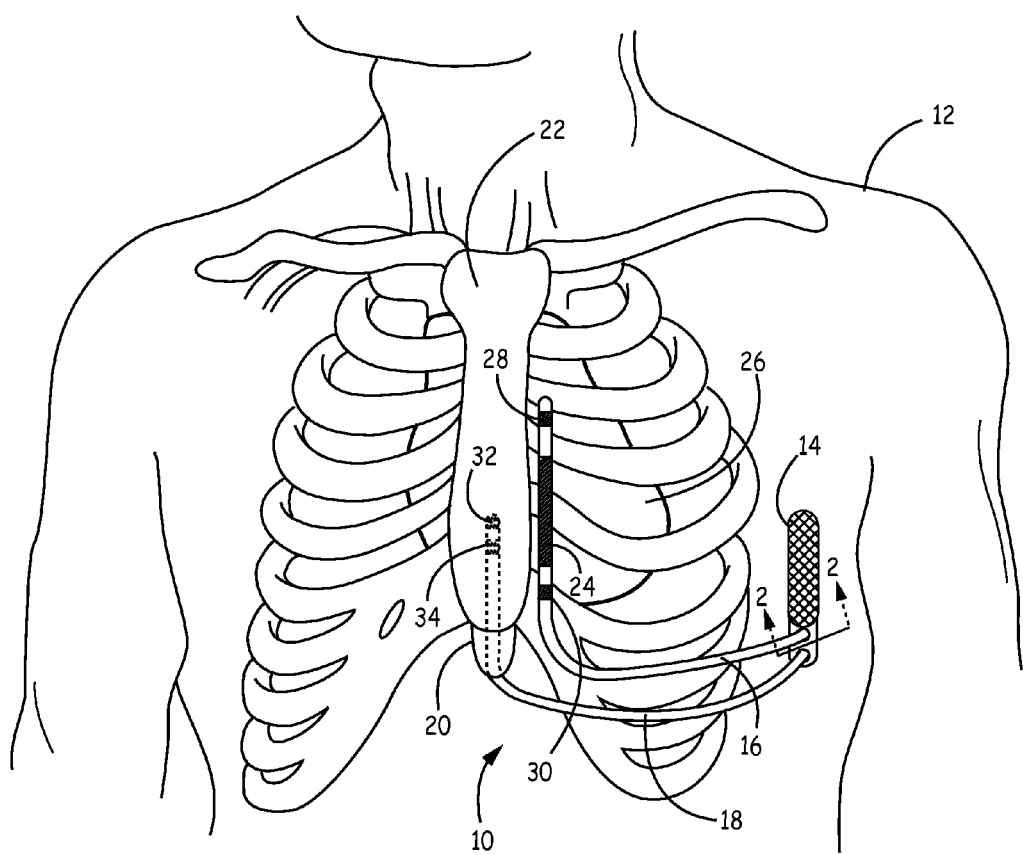
FIG. 1A is a front view of a patient implanted with implantable cardiac system having a substernal pacing lead.
Figure 1B:
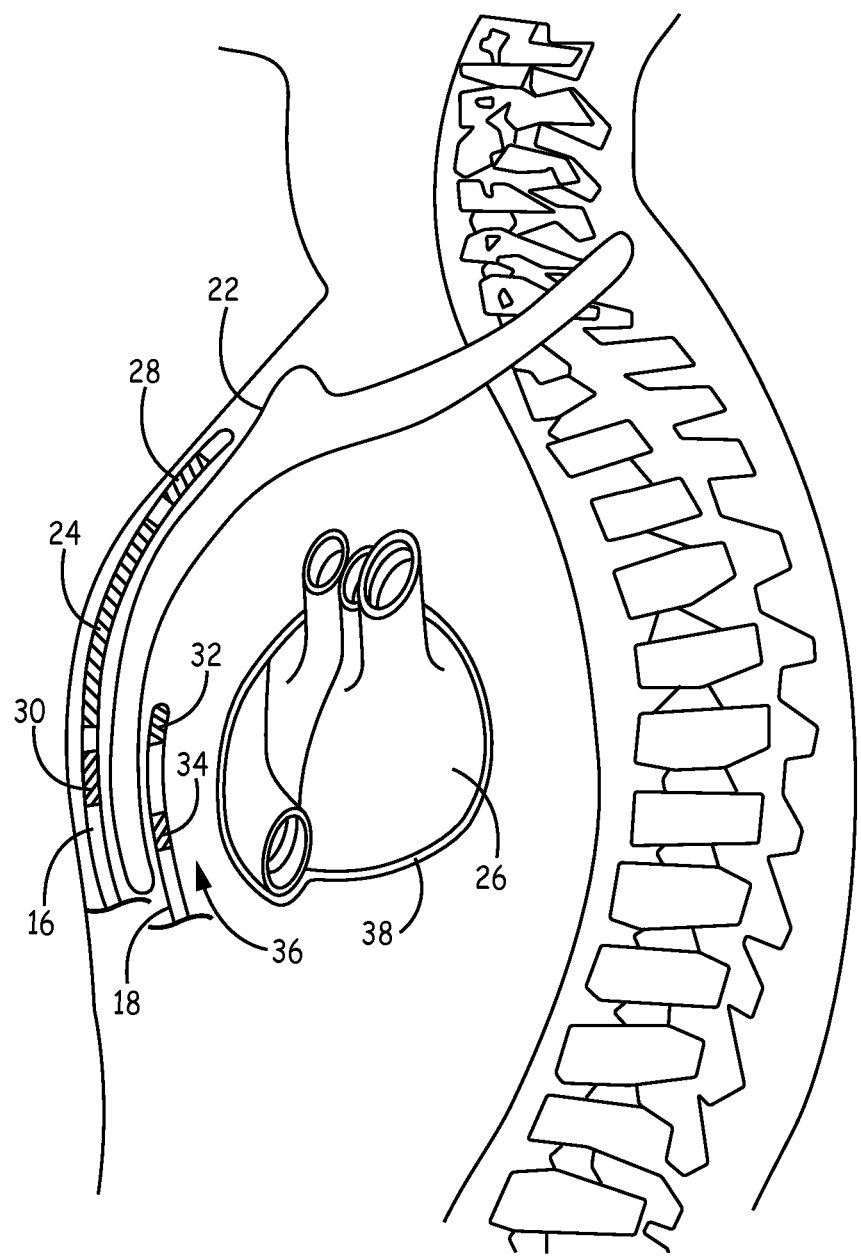
FIG. 1B is a side view of the patient with the implantable cardiac system having a substernal pacing lead.
Figure 1C:
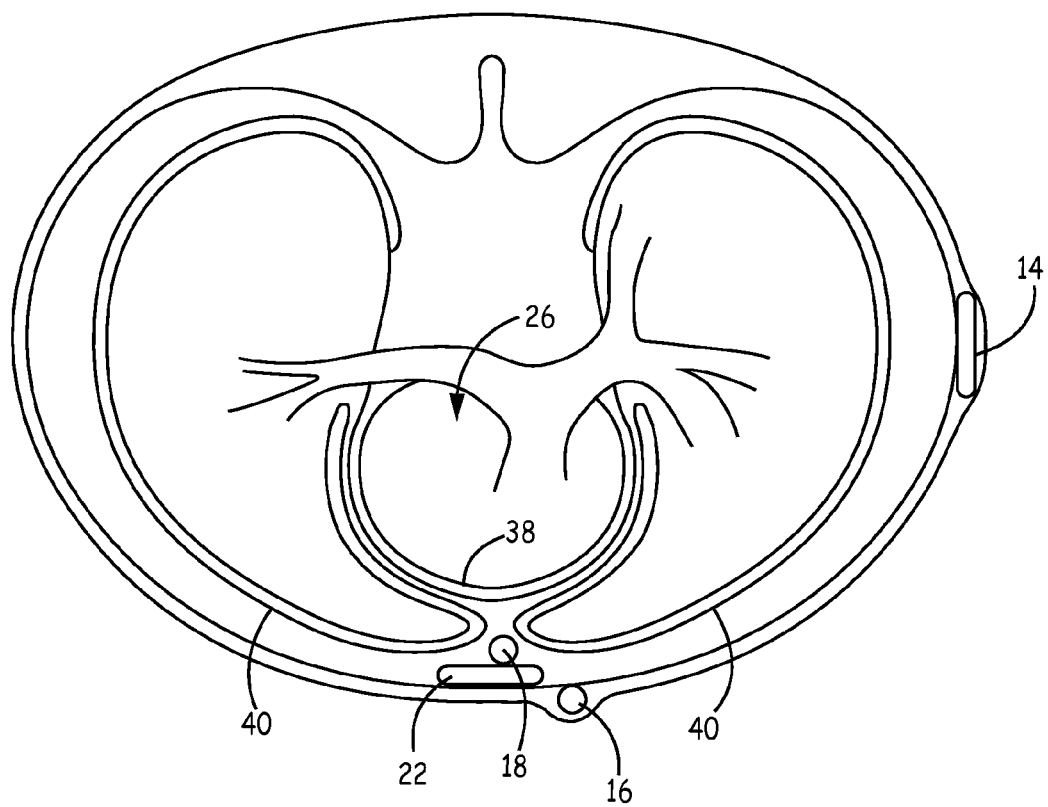
FIG. 1C is a transverse view of the patient with the implantable cardiac system having a substernal pacing lead.

FIGS. 1A-1C depict among other things an ICD and associated electrical lead system for providing cardiac sensing functions and therapy delivery functions, based on an operating mode selected from a plurality of modes. When operating under one of the operating modes, stimulation pulses may be applied to deliver a therapy to the patient in accordance with a programmed treatment regimen. Such therapy may include various known pacing and/or defibrillation therapies that are delivered in response to detection of various cardiac conditions by the ICD. In addition, the selected operating mode determines the sensing vectors that are utilized for sensing of signals indicative of a patient's cardiac electrical activity.

FIGS. 1A-C are conceptual diagrams of an implantable cardiac system 10 implanted within a patient 12. FIG. 1A is a front view of patient 12 implanted with implantable cardiac system 10. FIG. 1B is a side view of patient 12 with implantable cardiac system 10. FIG. 1C is a transverse view of patient 12 with implantable cardiac system 10.

Implantable cardiac system 10 includes an implantable medical device, in this example an ICD 14, connectable to one or more electrical leads such as defibrillation lead 16 and pacing lead 18. As will be described in more detail in FIG. 2, each of the electrical leads is connected to ICD 14 through separate lead connector ports that may be positioned, for example on a connector block located generally at the section through line 2-2. In the example illustrated in FIGS. 1A-C, ICD 14 is implanted subcutaneously on the left side of patient 12 above the ribcage. ICD 14 may, in some instances, be implanted between the left posterior axillary line and the left anterior axillary line of patient 12.

Defibrillation lead 16 includes a proximal end that includes a connector (not shown) configured to be connected to ICD 14 and a distal portion that includes electrodes 24, 28, and 30. Defibrillation lead 16 extends subcutaneously above the ribcage from ICD 14 toward a center of the torso of patient 12, e.g., toward xiphoid process 20 of patient 12. At a location near xiphoid process 20, defibrillation lead 16 bends or turns and extends superior subcutaneously above the ribcage and/or sternum, substantially parallel to sternum 22. Although illustrated in FIGS. 1A-C as being offset laterally from and extending substantially parallel to sternum 22, defibrillation lead 16 may be implanted at other locations, such as over sternum 22, offset to the right of sternum 22, angled lateral from sternum 22 at either the proximal or distal end, or the like.

Defibrillation lead 16 includes a defibrillation electrode 24 toward the distal portion of defibrillation lead 16, e.g., toward the portion of defibrillation lead 16 extending superior near sternum 22. Defibrillation lead 16 is placed along sternum 22 such that a therapy vector between defibrillation electrode 24 and a housing electrode of ICD 14 (or other second electrode of the therapy vector) is substantially across the ventricle(s) of heart 26. The therapy vector may, in one example, be viewed as a line that extends from a point on defibrillation electrode 24, e.g., center of defibrillation electrode 24, to a point on the housing electrode of ICD 14, e.g., center of the housing electrode. In one example, the therapy vector between defibrillation electrode 24 and the housing electrode of ICD 14 (or other second electrode of the therapy vector) is substantially across the right ventricle of heart 26.

Defibrillation electrode 24 is illustrated in FIG. 1A as being an elongated coil electrode. Defibrillation electrode 24 may vary in length depending on a number of variables. Defibrillation electrode 24 may, in one example, have a length of between approximately 5-10 centimeters (cm). However, defibrillation electrode 24 may have a length less than 5 cm and greater than 10 cm in other embodiments. Another example, defibrillation electrode 24 may have a length of approximately 2-16 cm.

In other embodiments, however, defibrillation electrode 24 may be a flat ribbon electrode, paddle electrode, braided or woven electrode, mesh electrode, segmented electrode, directional electrode, patch electrode or other type of electrode besides an elongated coil electrode. In one example, defibrillation electrode 24 may be formed of a first segment and a second segment separated by a distance and having at least one sensing electrode located between the first and second defibrillation electrode segments. In other embodiments, defibrillation lead 16 may include more than one defibrillation electrode. For example, defibrillation lead 16 may include a second defibrillation electrode (e.g., second elongated coil electrode) near a proximal end of lead 16 or near a middle of lead 16.

Defibrillation lead 16 also includes electrodes 28 and 30 located along the distal portion of defibrillation lead 16. In the example illustrated in FIGS. 1A-C, electrode 28 and 30 are separated from one another by defibrillation electrode 24. In other examples, however, electrodes 28 and 30 may be both distal of defibrillation electrode 24 or both proximal of defibrillation electrode 24. In instances in which defibrillation electrode 24 is a segmented electrode with two defibrillation segments, one or both electrodes 28 and 30 may be located between the two segments and, in some cases, lead 16 may include additional electrodes proximal or distal to the defibrillation segments.

Electrodes 28 and 30 may comprise ring electrodes, short coil electrodes, paddle electrodes, hemispherical electrodes, segmented electrodes, directional electrodes, or the like. Electrodes 28 and 30 of lead 16 may have substantially the same outer diameter as the lead body. In one example, electrodes 28 and 30 may have surface areas between 1.6-55 mm$^2$. Electrodes 28 and 30 may, in some instances, have relatively the same surface area or different surface areas. Depending on the configuration of lead 16, electrodes 28 and 30 may be spaced apart by the length of defibrillation electrode 24 plus some insulated length on each side of defibrillation electrode, e.g., approximately 2-16 cm. In other instances, such as when defibrillation electrodes 28 and 30 are between a segmented defibrillation electrode, the electrode spacing may be smaller, e.g., less than 2 cm or less than 1 cm. The example dimensions provided above are exemplary in nature and should not be considered limiting of the embodiments described herein. In other embodiments, defibrillation lead 16 may not include electrodes 28 and/or 30. In this case, defibrillation lead 16 would only include defibrillation electrode 24 and pacing lead 18 having sensing electrodes may be connected to ICD 14 for the sensing functions, as described further below. Alternatively, defibrillation lead 16 may include more than two pace/sense electrodes.

ICD 14 may obtain sensed electrical signals corresponding with electrical activity of heart 26 via a combination of sensing vectors that include combinations of electrodes 28 and/or 30 and the housing electrode of ICD 14. For example, ICD 14 may obtain electrical signals sensed using a sensing vector between electrodes 28 and 30, obtain electrical signals sensed using a sensing vector between electrode 28 and the conductive housing electrode of ICD 14, obtain electrical signals sensed using a sensing vector between electrode 30 and the conductive housing electrode of ICD 14, or a combination thereof. In some instances, ICD 14 may even obtain sensed electrical signals using a sensing vector that includes defibrillation electrode 24.

In some embodiments, defibrillator lead 16 may deliver pacing therapies in addition to providing cardioversion/defibrillation therapies. ICD 14 may be configured to provide pacing therapy via a combination of therapy vectors that include combinations of electrodes 24, 28, and/or 30, and the housing electrode of ICD 14. ICD 14 may deliver such pacing pulses to heart 26 via a pacing vector that includes any combination of one or two of electrodes 24, 28, and 30 and a housing electrode of ICD 14. For example, ICD 14 may deliver pacing pulses using a bipolar pacing vector between electrodes 24, 28, or 24, 30, or 28 and 30. In another example, ICD 14 may deliver pacing pulses using a unipolar pacing vector (e.g., between one of electrodes 24, 28, or 30 and the conductive housing electrode of ICD 14). In a further example, ICD 14 may deliver pacing pulses via pacing vector in which at least two of electrodes 24, 28, and 30 together form the cathode (or anode) of the pacing vector and the housing electrode of ICD 14 functions as the anode (or cathode) of the pacing vector.

As will be described in more detail with reference to defibrillator lead 16, ICD 14 may generate and deliver pacing pulses to provide anti-tachycardia pacing (ATP), bradycardia pacing, post-shock pacing, or other pacing therapies or combination of pacing therapies via pacing vectors formed using electrodes 24, 28, and/or 30 of the defibrillator lead 16.

Pacing lead 18 includes a proximal end that includes a connector configured to be connected to ICD 14 and a distal portion that includes electrodes 32 and 34. Pacing lead 18 extends subcutaneously above the ribcage from ICD 14 toward the center of the torso of patient 12, e.g., toward xiphoid process 20. At a location near xiphoid process 20, pacing lead 18 bends or turns and extends superior underneath/below sternum 22 in anterior mediastinum 36. Anterior mediastinum 36 may be viewed as being bounded laterally by pleurae 40, posteriorly by pericardium 38, and anteriorly by sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 18 extends along the posterior side of sternum 22 substantially within the loose connective tissue and/or substernal musculature of anterior mediastinum 36. A lead implanted with the distal portion substantially within anterior mediastinum 36 will be referred to herein as a substernal lead. Also, electrical stimulation, such as pacing, provided by a lead implanted with the distal portion substantially within anterior mediastinum 36 will be referred to herein as substernal electrical stimulation or substernal pacing.

Pacing lead 18 is implanted within anterior mediastinum 36 such that electrodes 32 and 34 are located near the ventricle of heart 26. For instance, the distal portion of pacing lead 18 may be implanted substantially within anterior mediastinum 36 such that electrodes 32 and 34 are located over a cardiac silhouette of the ventricle as observed via an anterior-posterior (AP) fluoroscopic view of heart 26. In one example, pacing lead 18 may be implanted such that one or both of a unipolar pacing vector from electrode 32 to a housing electrode of ICD 14 and/or a unipolar pacing vector from electrode 34 to the housing electrode of ICD 14 are substantially across the ventricles of heart 26. The therapy vector may again be viewed as a line that extends from a point on electrode 32 or 34, e.g., center of electrode 32 or 34, to a point on the housing electrode of ICD 14, e.g., center of the housing electrode. In another example, the spacing between electrodes 32 and 34 as well as the placement of pacing lead 18 may be such that a bipolar pacing vector between electrode 32 and electrode 34 is centered or otherwise located over the ventricle. However, pacing lead 18 may be positioned at other locations as long as unipolar and/or bipolar pacing vectors using electrodes 32 and 34 result in capture of the ventricle of the heart.

In the example illustrated in FIGS. 1A-C, pacing lead 18 is located substantially centered under sternum 22. In other instances, however, pacing lead 18 may be implanted such that it is offset laterally from the center of sternum 22. In some instances, pacing lead 18 may extend laterally enough such that all or a portion of the distal portion of pacing lead 18 is underneath/below the ribcage in addition to or instead of sternum 22 while still within the anterior mediastinum 22.

The distal portion of lead 18 is described herein as being implanted substantially within anterior mediastinum 36. Thus, points along the distal portion of lead 18 may extend out of anterior mediastinum 36, but the majority of the distal portion is within anterior mediastinum 36. In other embodiments, the distal portion of lead 18 may be implanted in other non-vascular, extra-pericardial locations, including the gap, tissue, or other anatomical features around the perimeter of and adjacent to, but not attached to, the pericardium or other portion of heart 26 and not above sternum 22 or ribcage. As such, lead 16 may be implanted anywhere within the "substernal space" defined by the undersurface between the sternum and/or ribcage and the body cavity but not including the pericardium. In this disclosure, the term "extra-pericardial" space refers to region around the outer heart surface, but not within the pericardial sac/space. The region defined as the extra-pericardial space includes the gap, tissue, bone, or other anatomical features around the perimeter of, and adjacent to the pericardium. The substernal space may alternatively be referred to by the terms "retrosternal space" or "mediastinum" or "infrasternal" as is known to those skilled in the art and includes the anterior mediastinum 36. The substernal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62 as Larrey's space. In other words, the distal portion of lead 18 may be implanted in the region around the outer surface of heart 26, but not attached to heart 26.

Pacing lead 18 includes an elongated lead body that contains one or more elongated electrical conductors (not illustrated) that extend within the lead body from the connector at the proximal lead end to electrodes 32 and 34 located along the distal portion of lead 18. The elongated lead body may have a generally uniform shape along the length of the lead body. In one example, the elongated lead body may have a generally tubular or cylindrical shape along the length of the lead body. The elongated lead body may have a diameter of between 3 and 9 French (Fr) in some instances. However, lead bodies of less than 3 Fr and more than 9 Fr may also be utilized. In another example, the distal portion (or all of) the elongated lead body may have a flat, ribbon or paddle shape. In this instance, the width across the flat portion of the flat, ribbon or paddle shape may be between 1 and 3.5 mm. The lead body of lead 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead body of lead 18 may engage with respective ones of electrodes 32 and 34. In one example, each of electrodes 32 and 34 is electrically coupled to a respective conductor within the lead body. The respective conductors may electrically couple to circuitry, such as circuits for controlling the low voltage or high voltage therapy of ICD 14 via connections in connector assembly, including associated feedthroughs. The electrical conductors transmit therapy from the circuits for controlling the low voltage or high voltage therapy that are within ICD 14 to one or more of electrodes 32 and 34 and transmit sensed electrical signals from one or more of electrodes 32 and 34 to the sensing cricuitry within ICD 14.

Electrodes 32 and 34 may comprise ring electrodes, hemispherical electrodes, coil electrodes, helix electrodes, segmented electrodes, directional electrodes, or other types of electrodes, or combination thereof. Electrodes 32 and 34 may be the same type of electrodes or different types of electrodes. In the example illustrated in FIGS. 1A-C electrode 32 is a hemispherical electrode and electrode 34 is a ring or coil electrode. Electrodes 32 and 34 of lead 18 may have substantially the same outer diameter as the lead body. In one example, electrodes 32 and 34 may have surface areas between 1.6-55 $mm^2$. In another example, one or both of electrodes 32 and 34 may be coil electrodes and may have surface areas of up to 200 $mm^2$. Electrodes 32 and 34 may, in some instances, have relatively the same surface area or different surface areas. For example, electrode 32 may have a surface area of approximately 2-5 $mm^2$ and electrode 34 may have a surface area between 15-44 $mm^2$.

In some instances, electrodes 32 and 34 may be spaced apart by approximately 5-15 mm. In other instances, electrodes 32 and 34 may be spaced apart by distances greater than 15 mm. For example, electrodes 32 and 34 may be spaced apart between 2-8 cm and still both be substantially over the ventricles. In another example, electrodes 32 and 34 may be spaced apart by greater than 8 cm, e.g., up to 16 cm apart, as may be the case to obtain atrial and ventricular pacing or sensing.

The example dimensions provided above are exemplary in nature and should not be considered as limiting of the embodiments described herein. In other examples, lead 18 may include a single electrode or more than two electrodes. In further examples, lead 18 may include one or more additional electrodes outside of the substernal space, e.g., near the apex of the heart or near a proximal end of lead 18.

ICD 14 may generate and deliver pacing pulses to provide anti-tachycardia pacing (ATP), bradycardia pacing, post-shock pacing, or other pacing therapies or combination of pacing therapies via pacing vectors formed using electrodes 32 and/or 34. The pacing therapy, whether it be ATP, post-shock pacing, bradycardia pacing, or other pacing therapy may be painlessly provided in an ICD system without entering the vasculature or the pericardial space, and without being attached to the heart. To the contrary, pacing therapy provided by a subcutaneous ICD system, if provided at all, is provided using pulse energies that may be uncomfortable for patient 12.

ICD 14 may deliver pacing pulses to heart 26 via a pacing vector that includes any combination of one or both of electrodes 32 and 34 and a housing electrode of ICD 14. For example, ICD 14 may deliver pacing pulses using a bipolar pacing vector between electrodes 32 and 34. In another example, ICD 14 may deliver pacing pulses using a unipolar pacing vector (e.g., between electrode 32 and the conductive housing electrode of ICD 14 or between electrode 34 and the conductive housing electrode of ICD 14). In a further example, ICD 14 may deliver pacing pulses via pacing vector in which electrodes 32 and 34 together form the cathode (or anode) of the pacing vector and the housing electrode of ICD 14 functions as the anode (or cathode) of the pacing vector. In still further instances, ICD 14 may deliver pacing therapy via a pacing vector between electrode 32 (or electrode 34) and an electrode of defibrillation lead 16, e.g., defibrillation electrode 24 or one of electrodes 28 or 30.

ICD 14 may also obtain sensed electrical signals corresponding with electrical activity of heart 26 via one or more sensing vectors that include combinations of electrodes 32 and 34 and/or the housing electrode of ICD 14. For example, ICD 14 may obtain electrical signals sensed using a bipolar sensing vector (e.g., between electrodes 32 and 34) or via a unipolar sensing vector (e.g., between electrode 32 and the conductive housing electrode of ICD 14 or between electrode 34 and the conductive housing electrode of ICD 14), or a combination thereof. In some instances, ICD 14 may obtain sensed electrical activity of heart 26 via a sensing vector between one of electrode 32 (or electrode 34) and electrodes 24, 28 and 30 of defibrillation lead 16. ICD 14 may deliver the pacing therapy based on the electrical signals sensed via the one or more of the sensing vectors of pacing lead 18. Alternatively or additionally, ICD 14 may deliver the pacing therapy based on the electrical signals sensed via the one or more of the sensing vectors of defibrillation lead 16 or based on both the electrical signals sensed via the sensing vector(s) of pacing lead 18 and defibrillation lead 16.

Pacing lead 18 may, in alternative embodiments, include more than two electrodes or only a single electrode. In instances in which pacing lead 18 includes more than two electrodes, ICD 14 may deliver pacing pulses and/or obtain sensed electrical signals of heart 26 via any of a number of combinations of the electrodes. For example, lead 18 may be a quadripolar lead having four ring electrodes toward a distal end of lead 18 and ICD 14 may deliver pacing pulses and/or sense electrical signals via any of the combinations of electrodes or between any one of the electrodes and the housing electrode of ICD 14.

ICD 14 analyzes the sensed electrical signals obtained from one or more of the sensing vectors of pacing lead 18 and/or one or more of the sensing vectors of defibrillation lead 16 to detect tachycardia, such as ventricular tachycardia or ventricular fibrillation. ICD 14 may analyze the heart rate and/or morphology of the sensed electrical signals to monitor for tachyarrhythmia in accordance with any of a number of techniques known in the art. One example technique for detecting tachyarrhythmia is described in U.S. Pat. No. 7,761, 150 to Ghanem et al., entitled "Method and Apparatus for Detecting Arrhythmias in a Medical Device," which is incorporated herein by reference in its entirety. Sensing may be completely performed via electrodes 32 and 34 of pacing lead 18 such that defibrillation lead 16 only includes a defibrillation electrode 24 and no sensing electrodes 28 or 30. In another example, ICD 14 may detect ventricular tachycardia or ventricular fibrillation using the signals sensed via electrodes 28 or 30 of defibrillation lead 16 and using the signals sensed via electrodes 32 or 34 of pacing lead 18 as a verification of the tachycardia or fibrillation.

In some instances, ICD 14 delivers one or more ATP therapies via the one or more pacing or therapy vectors of pacing lead 18 in response to detecting the tachycardia in an attempt to terminate the tachycardia without delivering a high voltage therapy, e.g., defibrillation shock or cardioversion shock. If the one or more ATP therapies are not successful or it is determined that ATP therapy is not desired, ICD 14 may deliver one or more cardioversion or defibrillation shocks via defibrillation electrode 24 of defibrillation lead 16. In other examples, ICD 14 may be configured to provide pacing therapy via a combination of therapy vectors that include combinations of the housing electrode of ICD 14, or one of electrodes 28 or 30 (or defibrillation electrode 24), and one of electrodes 32 or 34 of pacing lead 18. For example, ICD 14 may provide ATP and post-shock pacing using at least one electrode of defibrillation lead 16. In this case, lead 18 may be only utilized for sensing. In another example, ICD 14 may provide ATP using a therapy vector using an electrode of pacing lead 18 and deliver post-shock therapy using a therapy vector including an electrode of lead 16.

The configuration described above in FIGS. 1A-1C is directed to providing ventricular therapies via defibrillation lead 16 and pacing lead 18. In some instances, it may be desirable to provide atrial therapy in addition to or instead of ventricular therapy. In situations in which atrial pacing or sensing is desired in addition to or instead of ventricular pacing, pacing lead 18 may be positioned further superior. A pacing lead configured to deliver pacing pulses to both the atrium and ventricle may have more electrodes. For example, the pacing lead may have one or more electrodes located over a cardiac silhouette of the atrium as observed via the AP fluoroscopic view of heart 26 and one or more electrodes located over a cardiac silhouette of the ventricle as observed via the AP fluoroscopic view of heart 26. A pacing lead configured to deliver pacing pulses to only the atrium may, for example, have one or more electrodes located over a cardiac silhouette of the atrium as observed via the AP fluoroscopic view of heart 26. In some instances, a third lead (not shown) may further be connected to ICD 14. This third lead may, for example, function as an atrial pacing lead implanted such that the electrodes are located over a cardiac silhouette of the atrium as observed via the AP fluoroscopic view of heart 26.

Alternatively, it may be desirable to provide atrial therapies using defibrillation lead 16. In such a case, defibrillation lead 16 may include more than one defibrillation electrode and be placed further superior along sternum 22 such that a first therapy vector exists for the ventricle (e.g., via defibrillation electrode 24) and a second therapy vector exists for the atrium (e.g., via a second defibrillation electrode). In another example, defibrillation lead 16 may be placed further superior along sternum 22 such that a therapy vector between defibrillation electrode 24 and a housing electrode of ICD 14 is substantially across an atrium of heart 26, such that extravascular ICD system 10 may be used to provide atrial therapies to treat atrial fibrillation.

ICD 14 may include a housing that forms a hermetic seal that protects components of ICD 14. The housing of ICD 14 may be formed of a conductive material, such as titanium. ICD 14 may also include a connector assembly (also referred to as a connector block or header) that includes electrical feedthroughs through which electrical connections are made between conductors within leads 16 and 18 and electronic components included within the housing. As will be described in further detail herein, housing may house one or more processors, memories, transmitters, receivers, sensors, sensing circuitry, low and high voltage circuitry, power sources and other appropriate components. The housing is configured to be implanted in a patient, such as patient 12. Additionally, the housing also includes lead ports for connection of the leads as will be described in FIG. 2. Such lead ports may be formed anywhere on the housing, including on the connector assembly.

Like lead 18, lead 16 includes a lead body that contain one or more elongated electrical conductors (not illustrated) that extend through the lead body from the connector at a proximal lead end to the electrodes 24, 28, and 30. The lead bodies of leads 16 and 18 may be formed from a non-conductive material, including silicone, polyurethane, fluoropolymers, mixtures thereof, and other appropriate materials, and shaped to form one or more lumens within which the one or more conductors extend. The respective conductors may electrically couple to circuitry, such as circuits for controlling the low voltage or high voltage therapy of ICD 14 via the lead connection ports (FIG. 2), including associated feedthroughs. The electrical conductors transmit therapy from circuits for controlling the low voltage or high voltage therapy that are within ICD 14 to one or more of electrodes 24, 28, and 30 and transmit sensed electrical signals from one or more of electrodes 24, 28, and 30 to the sensing circuitry within ICD 14. However, the techniques are not limited to such constructions.

The leads 16 and 18 may further include one or more anchoring mechanisms that are positioned along the length of the lead body. The anchoring mechanisms affix the lead 18 that is implanted in a substernal space in a fixed location to prevent dislodging of the lead 18 once it is implanted. For example, the lead 18 may be anchored at one or more locations situated between the distal lead end positioned within the substernal space of patient 12 and a point along the length of the portion of the lead body at or near the insertion point of the lead body into the substernal space. The one or more anchoring mechanism(s) may either engage bone, fascia, muscle or other tissue of patient 12 or may simply be wedged therein to affix the lead under the sternum to prevent excessive motion or dislogment. In accordance with various embodiments, a portion or segment of the lead body may be formed with materials that function to encase conductors and other elements internal to the lead while also anchoring the lead within the implant environment.

The examples illustrated in FIGS. 1A-C are exemplary in nature and should not be considered limiting of the techniques described in this disclosure. In other examples, ICD 14, defibrillation lead 16, and pacing lead 18 may be implanted at other locations. For example, ICD 14 may be implanted in a subcutaneous pocket in the right pectoral region. In this example, defibrillation lead 16 may extend subcutaneously from the device toward the manubrium of the sternum and bend or turn and extend subcutaneously inferiorly from the manubrium of the sternum, substantially parallel with the sternum and pacing lead 18 may extend subcutaneously from the device toward the manubrium of the sternum to the desired location and bend or turn and extend inferior from the manubrium underneath/below sternum 22 to the desired location. In yet another example, implantable pulse generator 14 may be placed abdominally. Leads 16 and 18 may, in other examples be implanted at other locations on patient 12 as described, for example, in U.S. application Ser. No. 14/261,456 by Thompson-Nauman et al., entitled "Implantable Cardioverter-Defibrillator (ICD) System Including Substernal Pacing Lead," the contents of which are incorporated herein by reference in its entirety.

In accordance with embodiments of the invention, it is contemplated that additional leads, such as pacing lead 18, may be connected to the ICD 14 to deliver one or more therapies in conjunction with lead 16; or in the example of lead 18, to provide a separate therapy delivery function (in this case pacing).

In the example illustrated in FIGS. 1A-1C, system 10 is an ICD system that provides cardioversion/defibrillation and pacing therapy. However, these techniques may be applicable to other cardiac systems, including cardiac resynchronization therapy defibrillator (CRT-D) systems or other cardiac stimulation therapies, or combinations thereof. For example, ICD 14 may be configured to provide electrical stimulation pulses to stimulate nerves, skeletal muscles, diaphragmatic muscles, e.g., for various neuro-cardiac applications and/or for apnea or respiration therapy. In addition, it should be noted that system 10 may not be limited to treatment of a human patient. In alternative examples, system 10 may be implemented in non-human patients, e.g., primates, canines, equines, pigs, ovines, bovines, and felines. These other animals may undergo clinical or research therapies that may benefit from the subject matter of this disclosure.

Figure 2:
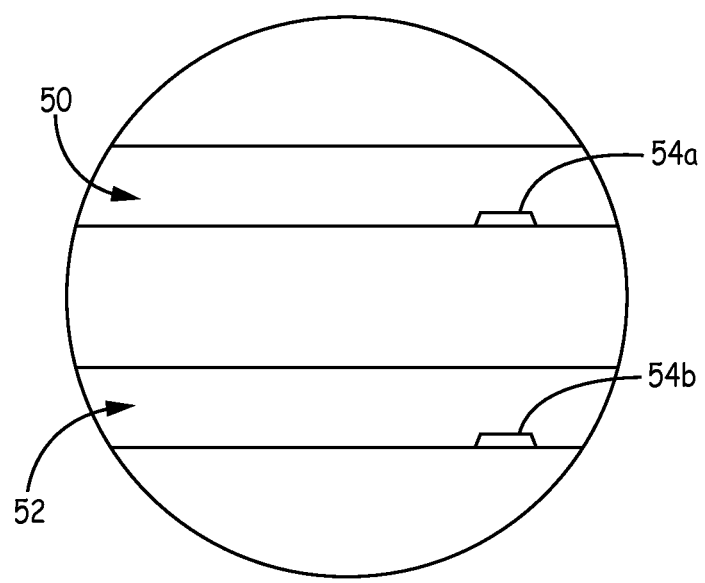
FIG. 2 is a cross-sectional view taken through line 2-2 of the implantable cardiac device shown in FIG. 1A.

FIG. 2 is a cross-sectional view taken though line 2-2 in FIG. 1A. Lead 16 is connectable to the ICD 14 through a defibrillation lead port 50 and the ICD 14 is configured for sensing and subcutaneous delivery of a defibrillation shock therapy, and/or optionally a pacing pulse therapy, to heart 26 through the lead 16. A pacing lead port 52 is provided for connection of lead 18 to the ICD 14 to be utilized for sensing and delivery of a pacing pulse therapy to heart 26.

The ICD 14 is configured to operate in a selected one of a plurality of modes, such as a multi-lead mode or a single lead mode. For example, in the single lead mode, the ICD 14 may be configured to operate without the pacing lead 18 being coupled to the pacing lead port, and to provide defibrillation shocks to the patient via the defibrillation lead 16. In another example of the single lead mode, the ICD 14 may be configured to operate without the defibrillation lead 16 being coupled to the defibrillation lead port, and to provide pacing pulse therapy to the patient via the pacing lead 18. The multi-lead modes may be defined as a function of the number of leads coupled to the device. For example, FIGS. 1A-1C illustrate a dual-lead mode whereby two leads 16 and 18 are coupled to the ICD 14. In a multi-lead mode, such as the dual-lead mode, the ICD 14 is configured to operate with both leads 16 and 18 coupled to the defibrillation lead port 50 and pacing lead port 52, respectively, and to provide pacing pulses to heart 26 of the patient 12 via the pacing lead 18 and provide defibrillation shocks to the patient via the defibrillation lead 16.

Therefore, the ICD 14 may be configured to recognize whether the defibrillation lead 16 and/or the pacing lead 18 is connected to the defibrillation lead port 50 and pacing lead port 52, respectively, and to assume or select either a single lead mode or multi-lead mode based on which of the leads 16 and/or 18 are connected. Alternatively, the ICD may be programmable to switch between the single lead and the multi-lead modes.

The defibrillation lead port 50 and the pacing lead port 52 may each include switches 54*a* and 54*b* (collectively "switches 54"). Switches 54 may be implemented as mechanical switches such as a flip switch, or an electro-mechanical switch, or an opto-mechanical switch, or a magnetic switch. Other examples of the switches 54 may include contactless switches such at that described in U.S. Pat. No. 6,612,404 to Sweet et al., entitled, "Contactless Hall Effect Push Button Switch," which is incorporated herein by reference in its entirety. However, the disclosure is not limited to the exemplary switches mentioned herein. Rather, the selection of the switch is predicated on the characteristics of the switch to generate a discernible signal upon insertion of a lead into the port.

The switch 54*a* is actuated or toggled from an open position to a closed position by the defibrillation lead 16 in response to insertion of the defibrillation lead 16 into the defibrillation lead port. Similarly, the switch 54*b* is toggled from an open position to a closed position by the pacing lead 18 in response to insertion of the pacing lead 18 into the pacing lead port. As will be described in more detail below, the actuation of switches 54 generates connection signals that will trigger the ICD 14 to function in a given one of the operating modes. The connection signal associated with each of the switches 54a, 54b may be an electrical signal that includes a unique identifier to enable the distinction between the signals generated by each of the switches. For example, modulation of the signal waveform may be employed to vary the characteristics of each signal.

Figure 3:
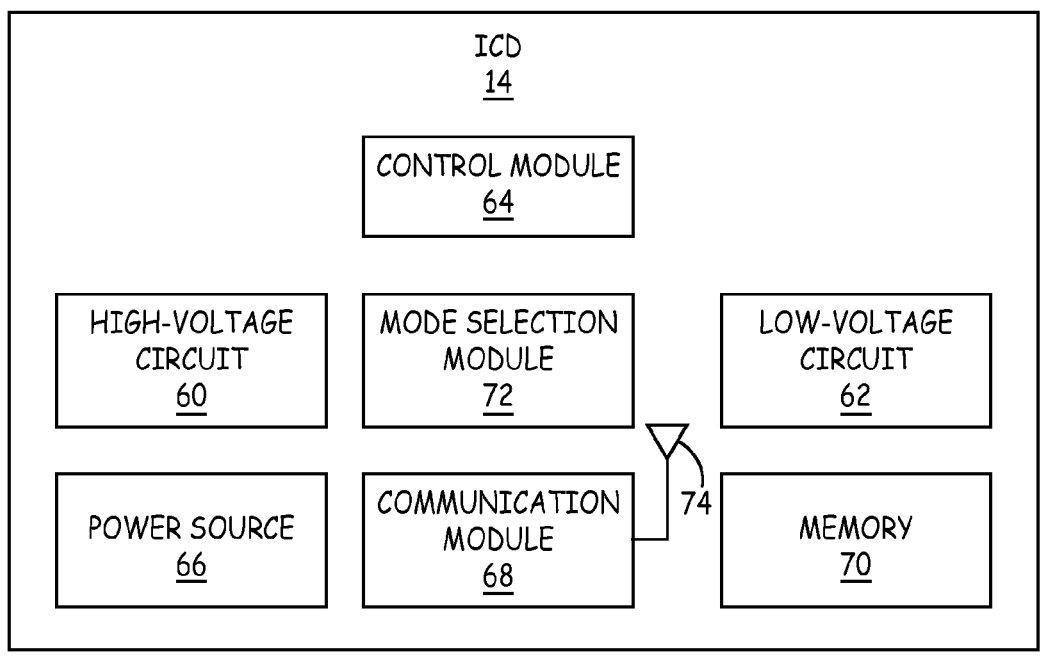
FIG. 3 is a block diagram of the circuitry of the implantable cardiac device shown in FIG. 1A.

FIG. 3 is a block diagram of the circuitry of ICD 14 in which the present invention may usefully be practiced. The circuitry depicted in FIG. 3 is exemplary of a circuit that may function to enable selective operation of the ICD 14 in one of several operating modes such that one or more of the pace, sense, and cardioversion/defibrillation functions are enabled based on the available leads.

The circuitry of ICD 14 includes a high voltage circuit 60 for generating relatively high voltage cardioversion/defibrillation shock therapies when needed, a low voltage circuit 62 for generating relatively low voltage pacing therapies. The therapies generated by the high voltage circuit 60 and the low voltage circuit 62 may be generated in response to detection of various cardiac maladies, such as a tachyarrhythmia, as determined from sensed P-waves and/or R-waves. Both the high voltage circuit 60 and the low voltage circuit 62 are operated under the control of a control module 64. The circuitry further includes a communication module 68, memory 70, a mode-selection module 72, and an antenna 74. The circuitry of ICD 14 receives power from a power source 66, which may, for example, be a rechargeable or non-rechargeable battery.

Mode-selection module 72 is coupled to both the high voltage circuit 60 and the low voltage circuit 62. Mode-selection module 72 is provided to selectively activate one or both of the voltage circuits 60 and/or 62 dependent on the selected operating mode of the ICD 14. In other words, the activation by mode-selection module 72 will be selected between the high voltage circuit 60 and the low voltage circuit 62. The operating modes may include a multi-lead mode, or a single lead mode, such for example as a pacing mode or a defibrillation mode or a combined pacing/defibrillation mode. As will be discussed in more detail below, the selective activation of one or both of the voltage circuits 60, 62 by mode-selection module 72 is based on the detection of the connection of leads 16, 18 to the ICD 14.

The high voltage circuit 60 and the low voltage circuit 62 generate stimulation energy that is delivered by the defibrillation lead 16 and to the pacing lead 18. The electrodes 24, 28, 30, 32, and 34 are coupled to the high voltage circuit 60 and the low voltage circuit 62 through conductors of the respective leads 16 and 18. Voltage circuits 60, 62 deliver therapy to heart 26 via one or more combinations of electrodes 24, 28, 30, 32, 34, and the housing electrode of ICD 14. Control module 64 controls the voltage circuits 60, 62 to generate electrical stimulation therapy with the amplitudes, pulse widths, timing, frequencies, or electrode combinations specified by the selected therapy program.

Voltage circuits 60, 62 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, voltage circuits 60, 62 may include a first set of components configured to provide pacing therapy and a second set of components configured to provide defibrillation therapy. In other instances, the same set of components may be configurable to provide both pacing and defibrillation therapy. In still other instances, some of the defibrillation and pacing therapy components may be shared components while others are used solely for defibrillation or pacing.

The components of the high voltage circuit 60 and the low voltage circuit 62 may include analog components, digital components or a combination thereof. Such components may include one or more sense amplifiers, filters, rectifiers, threshold detectors, analog-to-digital converters (ADCs) or the like. Electrical signals indicative of cardiac activity may be sensed by the voltage circuits 60 and/or 62 and provided in digital form to control module 64 for processing or analysis. For example, voltage circuits 60, 62 may amplify raw analog signals from the sensing electrodes and convert the amplified signals to multi-bit digital signals by an ADC. The processed signals may be compared to a threshold to detect the existence of atrial or ventricular depolarizations (e.g., P- or R-waves) and indicate the existence of the atrial depolarization (e.g., P-waves) or ventricular depolarizations (e.g., R-waves).

Control module 64 may process the sensed signals to monitor electrical activity of heart 26 of patient 12. Control module 64 may store the sensed signals as well as any generated EGM waveforms, marker channel data or other data derived based on the sensed signals in memory 70. Control module 64 also analyzes the EGM waveforms and/or marker channel data to detect cardiac events (e.g., tachycardia). In response to detecting the cardiac event, control module 64 may control one or both voltage circuits 60, 62 to generate and deliver the desired one or more therapy programs, which may be stored in memory 70 according to a treatment regimen of the patient 12. The therapy may include, but is not limited to, defibrillation or cardioversion shock(s), ATP, post-shock pacing, bradycardia pacing, or the like.

In the case of pacing therapy, e.g., ATP, post-shock pacing, and/or bradycardia pacing, provided via electrodes 32 and/or 34 of pacing lead 18, control module 64 controls low voltage circuit 62 to generate and deliver pacing pulses with any of a number of amplitudes and pulse widths to capture heart 26. The pacing thresholds of heart 26 when delivering pacing pulses from the anterior mediastinum using pacing lead 18 may depend upon a number of factors, including location, type, size, orientation, and/or spacing of electrodes 32 and 34, location of ICD 14 relative to electrodes 32 and 34, physical abnormalities of heart 26 (e.g., pericardial adhesions or myocardial infarctions), or other factor(s).

The increased distance from electrodes 32 and 34 of pacing lead 18 to the heart tissue may result in heart 26 having increased pacing thresholds compared to transvenous pacing thresholds. To this end, low voltage circuit 62 may be configured to generate and deliver pacing pulses having larger amplitudes and/or pulse widths than conventionally required to obtain capture via transvenously implanted lead or a lead attached to heart 26. In one example, low voltage circuit 62 may generate and deliver pacing pulses having amplitudes of less than or equal to 8 volts and pulse widths between 0.5-3.0 milliseconds. In another example, low voltage circuit 62 may generate and deliver pacing pluses having amplitudes of between 5 and 10 volts and pulse widths between approximately 3.0 milliseconds and 10.0 milliseconds. In another example, low voltage circuit 62 may generate and deliver pacing pluses having pulse widths between approximately 2.0 milliseconds and 8.0 milliseconds. In a further example, low voltage circuit 62 may generate and deliver pacing pluses having pulse widths between approximately 0.5 milliseconds and 20.0 milliseconds. In another example, low voltage circuit 62 may generate and deliver pacing pluses having pulse widths between approximately 1.5 milliseconds and 20.0 milliseconds.

In some cases, low voltage circuit 62 may generate pacing pulses having longer pulse durations than conventional transvenous pacing pulses to achieve lower energy consumption. For example, low voltage circuit 62 may be configured to generate and deliver pacing pulses having pulse widths or durations of greater than two (2) milliseconds. In another example, low voltage circuit 62 may be configured to generate and deliver pacing pulses having pulse widths or durations of between greater than two (2) milliseconds and less than or equal to three (3) milliseconds. In another example, low voltage circuit 62 may be configured to generate and deliver pacing pulses having pulse widths or durations of greater than or equal to three (3) milliseconds. In another example, low voltage circuit 62 may be configured to generate and deliver pacing pulses having pulse widths or durations of greater than or equal to five (5) milliseconds. In another example, low voltage circuit 62 may be configured to generate and deliver pacing pulses having pulse widths or durations of greater than or equal to ten (10) milliseconds. In a further example, low voltage circuit 62 may be configured to generate and deliver pacing pulses having pulse widths between approximately 3-10 milliseconds. In a further example, low voltage circuit 62 may be configured to generate and deliver pacing pulses having pulse widths or durations of greater than or equal to fifteen (15) milliseconds. In yet another example, low voltage circuit 62 may be configured to generate and deliver pacing pulses having pulse widths or durations of greater than or equal to twenty (20) milliseconds.

Depending on the pulse widths, ICD 14 may be configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. Typically the lower amplitudes require longer pacing widths. Reducing the amplitude of pacing pulses delivered by ICD 14 reduces the likelihood of extra-cardiac stimulation.

In the case of defibrillation therapy, e.g., defibrillation or cardioversion shocks provided by defibrillation electrode 24 of defibrillation lead 16, control module 64 controls high voltage circuit 60 to generate defibrillation or cardioversion shocks having any of a number of waveform properties, including leading-edge voltage, tilt, delivered energy, pulse phases, and the like. High voltage circuit 60 may, for instance, generate monophasic, biphasic or multiphasic waveforms. Additionally, high voltage circuit 60 may generate defibrillation waveforms having different amounts of energy. For example, high voltage circuit 60 may generate defibrillation waveforms that deliver a total of between approximately 60-80 Joules (J) of energy. High voltage circuit 60 may also generate defibrillation waveforms having different tilts. In the case of a biphasic defibrillation waveform, high voltage circuit 60 may use a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide subcutaneous defibrillation via defibrillation electrode 24.

Communication module 68 includes any suitable hardware, firmware, software or any combination thereof for communicating with another device, such as a clinician programmer, a patient monitoring device, or the like. For example, communication module 68 may include appropriate modulation, demodulation, frequency conversion, filtering, and amplifier components for transmission and reception of data with the aid of antenna 74. Antenna 74 may be located within the connector block of ICD 14 or within housing ICD 14.

The modules 60-72 in FIG. 3 may be implemented together on a common hardware component or separately as discrete but interoperable hardware, firmware or software components. Depiction of different features as circuits/modules is intended to highlight different functional aspects and does not necessarily imply that such circuits/modules must be realized by separate hardware, firmware or software components. Rather, functionality associated with one or more circuits/modules may be performed by separate hardware, firmware or software components, or integrated within common or separate hardware, firmware or software components.

Moreover, the various modules of ICD 14 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. For example, the control module 64 is generally representative of a processor and associated memory. Such memory components, including, for example, memory 70 may include computer readable instructions that, when executed by a processor, cause the components of the ICD 14 to perform various functions attributed to those components, such as the functions described in this disclosure. For example, the memory may include any non-transitory, computer-readable storage media including any combination of one or more of a volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

FIG. 3 should be taken as exemplary of the type of operational circuitry that is included in ICD 14, it being understood that the functionality provided by the operational circuitry will be activated based on the available leads.

By way of example, the Table 1 that is shown below summarizes the functions of the ICD 14 under various operating modes based on the available lead(s).

TABLE 1

| MODE | CONNECTED LEAD | OPERATING MODE |
|---|---|---|
| D1 | Defibrillation Lead | Single Lead Mode (Sensing, Defibrillation Therapies) |
| D2 | Defibrillation Lead | Single Lead Mode (Sensing, Pacing & Defibrillation Therapies) |
| P1 | Pacing Lead | Single Lead Mode (Sensing, Pacing Therapies) |
| M1 | Pacing and Defibrillation Leads | Multi-Lead Mode (Sensing, Pacing and Defibrillation Therapies) |

With reference to FIG. 1A, the electrodes 24, 28, 30, 32, and 34 are coupled to the high voltage circuit 60 and the low voltage circuit 62 through conductors of the respective leads 16 and 18. As such, the sensing and therapy delivery functions described above may be selectively activated as outlined in Table 1 based on the connection of the leads 16, 18. To achieve the selective activation, the control module 64 will select between Mode D1, Mode D2, Mode P1, and Mode M1 based on the determination of which lead(s) is/are connected. For example, assuming the electrode configuration of FIGS. 1A, 1B and 1C, the correspondence to the illustrated leads 16 and 18 to the voltage circuits 60, 62 is as follows. When lead 16 is connected to the ICD 14, the high voltage circuit 60 is activated to sense electrical signals indicative of cardiac activity and/or provide cardioversion/defibrillation therapy via electrodes 24, 28, and 30 (Mode D1). In alternative embodiments, both the high voltage circuit 60 and the low voltage circuit 62 may be activated in response to connection of only lead 16 (Mode D1). In some embodiments, the activation of the low voltage circuit 62 in the D2mode for pacing therapies may be performed manually such as through an external programmer. In such embodiments, the ICD 14 will default to the D1mode if lead 16, but not lead 18, is connected. Subsequently, if the D2mode is desired, a user such as a clinician will manually select that operating mode. When only lead 18 is connected to the ICD 14, the low voltage circuit 62 may be activated to sense electrical signals indicative of cardiac activity and/or provide pacing therapy via electrodes 32, 34 (Mode P1). In yet another example, both the high voltage circuit 60 and the low voltage circuit 62 may be activated in response to connection of both lead 16 and lead 18 (Mode M1).

For various reasons, it may be desirable to identify the number and/or type of leads that are coupled to ICD 14. For instance, embodiments of the present disclosure are directed to configuring the ICD 14 for operation in one operating mode that is selected from several operating modes, such as the exemplary D1, D2, P1, and M1 modes outlined in Table 1. To that end, an identification of the connection of one or both leads 16, 18 will trigger the selection of an operating mode of ICD 14.

In one exemplary embodiment, the switches 54 are utilized to determine the presence of one or both leads 16 and 18. The switches 54 are electrically coupled to control module 64 for transmission of connection signals that are indicative of actuation of the switches. For example, a connection signal may be generated in response to toggling the switches from the open position to the closed position, with the toggling being triggered by insertion of a lead (e.g., 16, or 18) into a port (e.g., 50, or 52). The control module 64 determines which one of the lead 16 or lead 18 has been connected based on the characteristics of the received connection signals. In response to determining which of the leads 16, 18 is connected, control module 64 generates a mode signal that is transmitted to the mode-selection module 72. The connection signal transmitted due to actuation of a given one or both of switches 54a, 54b will trigger the control module 64, and hence the ICD 14, to function in an operating mode as determined, for example, in Table 1 above. Accordingly, the mode signal controls the mode-selection module 72 to selectively activate one or both of the high voltage circuit 60 and the low voltage circuit 62. For example, mode-selection module 72 selectively activates one of the high voltage circuit 60 or the low voltage circuit 62 in a single lead mode, or both of the high voltage circuit 60 and the low voltage circuit 62 in a multi-lead mode.

In another embodiment, the determination of whether one or both of leads 16, 18 is/are coupled to ICD 14 may be based on connection signals generated from the result of a lead recognition evaluation. An example of the lead recognition evaluation may include impedance measurements of lead paths utilizing each of the lead ports 50, 52. Lead impedance measurements are known in the art. For example, control module 64 may utilize the lead impedance measurement techniques described in U.S. Pat. No. 8,644,931 to Stadler et al., entitled, "Impedance Variability Analysis to Identify Lead-Related Conditions," which issued on Feb. 4, 2014, or in U.S. Pat. No. 5,897,577 to Cinbis et al., entitled, "Pacing Lead Impedance Monitoring Circuit and Method," which issued on Apr. 27, 1999, or in U.S. Pat. No. 5,755,742 to Gering et al., entitled, "Cardioversion/Defibrillation Lead Impedance Measurement System" which issued on May 26, 1998, all of which are incorporated herein by reference in their entireties.

The results of the lead impedance measurements may be utilized to determine whether or not one or both of leads 16, 18 are connected to the ICD 14. For example, it may be assumed that an operable lead should have an impedance in a predetermined range, such as between 15 ohms ($\Omega$) to 200$\Omega$. If an impedance value outside of this predetermined range is measured for a lead path including a given port, a determination is made that the lead 16 or 18 is not connected to the respective lead port 50 or 52. Based on the result, the control module 64 generates a mode signal that is transmitted to the mode-selection module 72 for selective activation of one or both of the high voltage circuit 60 and the low voltage circuit 62.

The mode signal generated by the control module 64 as a function of the results of the impedance measurement or as a function of the actuation of switches 54 triggers the control module 64 to select an operating mode to control the functions of the ICD 14. For example, if the result of the impedance measurements for the path defined by lead 16 is outside the predetermined range, the control module 64 determines that lead 16 is not connected to the ICD 14. Therefore, the high voltage circuit 60 may be inactivated based on the mode signal issued by control module 64. Continuing with the example, once lead 16 has been connected (either at the initial implantation or subsequently), the impedance measurement will result in an impedance result that is within the predetermined range. Once so detected, the lead 16 is indicated as being "present" within the system. Thereafter, ICD 14 will always assume the presence of lead 16 until or unless it is reset, e.g., by a command received from an external programmer. Also, once the lead 16 is found to be present, high voltage circuit 60 is activated and ICD 14 will enable the functions that are dependent upon lead 16 being present. For example, the ICD 14 may assume or select one of operating modes D1 or D2. Alternatively, one of the D1 or D2 operating modes may be availed as a programmable mode upon confirmation by the ICD 14 that the lead 16 is present.

In a manner similar to the foregoing, the operating mode P1 or M1 and the functions that are dependent upon pacing lead 18 will be activated based on a determination of whether lead 18 is present.

Figure 4:
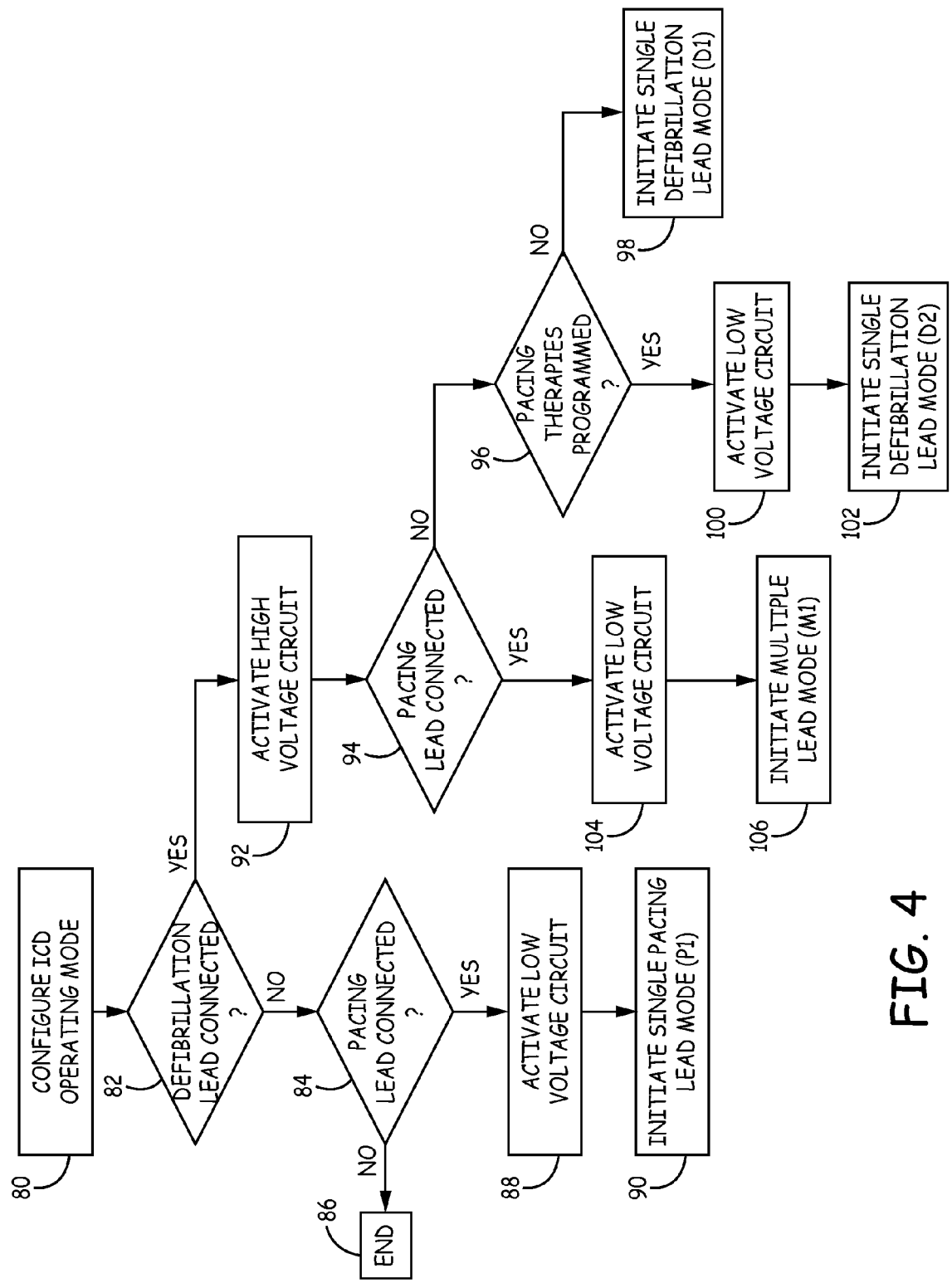
FIG. 4 is a flowchart illustrating a method of selectively-operating an ICD in one of a plurality of operating modes.

FIG. 4 is a flowchart illustrating a method of selectively-operating an ICD in one of a plurality of operating modes. The tasks of the method will be described in conjunction with the above-described system that includes ICD 14 and leads 16 and 18. As explained above, only one of leads 16, 18 may be connected to the ICD 14, and therefore the ICD 14 will monitor the lead ports for the connected leads and select an operating mode based on the number and/or type of leads that are connected. The exemplary operating modes described in FIG. 4, correspond to those outlined in Table 1.

At a predetermined time, a configuration routine is initialized to configure the ICD 14 (task 80). The configuration routine may be initialized during the initial setup of the ICD 14, such as during manufacturing, or preferably during an implant procedure. The configuration routine may also be performed at periodic intervals such as daily, or weekly, or monthly during the operating lifetime of the device. The calibration routine will include selecting an operating mode under which the ICD 14 will perform sensing and therapy delivery functions.

To that end, methods in accordance with embodiments of the disclosure include evaluating whether defibrillation lead 16 is connected to the ICD 14 (82). The monitoring and detection techniques used to determine the presence of defibrillation lead 16 may include the lead recognition evaluation and the activation of switch 54*a* that is associated with the lead port 50 as described herein. If the defibrillation lead 16 is not present, an assessment is subsequently made as to whether a pacing lead 18 is connected to the ICD 14 (84). The method may utilize the monitoring and detection techniques described above to determine whether the pacing lead 18 is connected to lead port 52. If the pacing lead is not connected, the configuration of the operating modes is terminated (86) and none of the operating modes are selected. The ICD 14 may issue an alert to inform the user, such as a clinician or patient that none of the leads 16, 18 are connected to the ICD 14. Such an alert may be in the form of an audible tone or other appropriate warning indicia.

If it is determined that the pacing lead 18 is connected, the ICD 14 will activate the low voltage circuit 62 that is coupled to the pacing lead (88). The ICD 14 will select the single lead mode P1 and the sensing and therapy delivery functions will be performed under control of the single pacing lead mode (90). Based on selection of the single pacing lead mode P1 as the operating mode, the low voltage circuit 62 senses electrical signals indicative of cardiac activity and/or provides pacing therapy via electrodes 32, 34.

Referring back to task 82, in response to detecting that defibrillation lead 16 is connected to the lead port 50, the method activates the high voltage circuit (92). Next, a determination is made as to whether the pacing lead 18 is connected to the ICD 14 (task 94). In response to determining that the pacing lead 18 is not connected, the method further includes an assessment as to whether the predetermined treatment regimen of the patient includes delivery of pacing therapies (96). For example, a user such as a clinician may desire to provide a treatment regimen for patient 12 that includes pacing therapies, whether a pacing lead is present or not. Accordingly, if the ICD 14 determines that the programmed treatment regimen does not include pacing, or if there are no programmed instructions to provide pacing off the defibrillation lead, or if the defibrillation lead does not support pacing, the ICD 14 may in one embodiment select the single lead mode D1 as the operating mode (98). As such, the sensing and cardioversion/defibrillation therapy delivery functions will be performed under this defibrillation mode.

Otherwise, if the assessment at task 96 indicates that pacing therapies are desired, the ICD 14 will activate the low voltage circuit (100) for delivery of the pacing therapies through the defibrillation lead 16. The ICD 14 will further select the single lead mode D2 as the appropriate operating mode (102). Based on selection of mode D2 as the operating mode, the high voltage circuit 60 and low voltage circuit 62 are operated to sense electrical signals indicative of cardiac activity and/or provide pacing, cardioversion/defibrillation therapies via electrodes 24, 28, and 30.

Returning to task 94, in response to determining that the pacing lead 18 is connected, the low voltage circuit 62 is activated (104). The determination that both the defibrillation lead 16 and the pacing lead 18 are connected to ICD 14 triggers selection of a multi-lead mode, mode M1 (106). Based on the selection of the multi-lead mode M1 as the operating mode, the high voltage circuit 60 functions to provide cardioversion/defibrillation therapy via electrodes 24, 28, and 30, while the low voltage circuit 62 functions to provide pacing therapy via electrodes 32, 34. Additionally, the high voltage circuit 60 and/or the low voltage circuit 62 may be utilized to sense electrical signals indicative of cardiac activity via one or more sensing vectors that are defined by electrodes 24, 28, 30, 32, and 34.

It is also contemplated that the ICD 14 may switch from the multi-lead mode of operation to one of the single lead modes, such as the single pacing lead mode or the single defibrillation lead mode, depending on a determination of which lead(s) is/are connected. For example, the method may determine that one or more of leads 16, 18 is/are inoperative or not connected to the appropriate lead port. Such a determination triggers the ICD 14 to switch operating modes and reconfigure the sensing and therapy delivery functions based on the available leads. In one instance, the operating mode may switch from the multi-lead mode of operation when both defibrillation lead 16 and pacing lead 18 are connected to a single lead mode such as D1, or D2, or P1 based on identification of a lead-related condition associated with one of the connected leads 16, 18. Doing so will ensure that an inoperative lead is no longer relied upon.

The disclosure has been described in terms of defibrillation lead 16 and pacing lead 18, it being understood that the invention is not limited to only two leads. Rather, the invention is usefully employed in systems having more than two leads of various types such that additional single and multi-lead operating modes may be defined as a function of the leads that are connected to the ICD 14.

Accordingly, various techniques, circuits and methods have been described for identifying the lead/electrode combinations associated with a medical device and configuring the functionality of the IMD according to the lead(s) connected to the medical device.

As used in the description and the claims, the phrase "one of . . . , and . . . " or the phrase "at least one of . . . , and . . . " when combined with a list of items, means a single item from the list or any combination of items in the list. For example, "at least one of the first connection signal and the second connection signal" means "only the first connection signal, or only the second connection signal, or the first connection signal and the second connection signal." The phrase "select between . . . , and . . . " when combined with a list of items, means making a selection of one item from a list of items, and therefore, each of the items in the list has to be present for a selection to be made. For example, "select between a single lead mode and a multi-lead mode" means that at least one single lead mode is present and at least one multi-lead mode is present, each of the single lead mode(s) and the multi-lead mode(s) being distinguishable by the ICD 14. Continuing with that example, the "selection between a single lead mode and a multi-lead mode" involves selecting one of the single lead mode(s) or one of the multi-lead mode(s).

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. It should also be understood that various changes can be made in the function and arrangement of elements without departing from the scope of the disclosure as set forth in the appended claims and the legal equivalents thereof.

What is claimed is:

1. An implantable medical device (IMD) system comprising:
    a housing having a defibrillation lead port and a pacing lead port;
    a defibrillation lead configured to be connected to the defibrillation lead port;
    a pacing lead configured to be connected to the pacing lead port;
    a control module operable to receive a first connection signal indicative of a connection of the defibrillation lead to the defibrillation lead port and a second connection signal indicative of a connection of the pacing lead to the pacing lead port, wherein the first connection signal differs from the second connection signal and the control module generates a mode signal triggered by receipt of at least one of the first connection signal and the second connection signal;
    a high voltage circuit coupled to the control module and operable to generate a defibrillation shock therapy;
    a low voltage circuit coupled to the control module and operable to generate a pacing pulse therapy; and
    a mode-selection module configured to select between a single lead mode and a multi-lead mode based on the mode signal generated by the control module.

2. The IMD system of claim 1, further comprising a first switch coupled to the defibrillation lead port that is actuated responsive to connection of the defibrillation lead and a second switch coupled to the pacing lead port that is actuated responsive to connection of the pacing lead, wherein the first connection signal is generated in response to actuation of the first switch and wherein the second connection signal is generated in response to actuation of the second switch.

3. The IMD system of claim 1, wherein the mode-selection module selectively activates at least one of the high voltage circuit and the low voltage circuit based on the mode signal.

4. The IMD system of claim 3, wherein the mode-selection module selectively activates:
    one of the high voltage circuit or the low voltage circuit during operation in the single lead mode, or
    both the high voltage circuit and the low voltage circuit during operation in the multi-lead mode.

5. The IMD system of claim 1, wherein the control module is configured to initiate a lead recognition determination, wherein:
    the first connection signal is generated in response to a result of the lead recognition determination indicating that the defibrillation lead is connected to the defibrillation lead port, and
    the second connection signal is generated in response to a result of the lead recognition determination indicating that the pacing lead is connected to the pacing lead port.

6. The IMD system of claim 5, wherein the lead recognition determination comprises an impedance measurement of a pathway including the defibrillation lead port, and the result is indicative of connection of the defibrillation lead to the defibrillation lead port if a value of the lead impedance measurement is within a predetermined range.

7. The IMD system of claim 5, wherein the lead recognition determination comprises an impedance measurement of a pathway including the pacing lead port, and the result is indicative of connection of the pacing lead to the pacing lead port if a value of the lead impedance measurement is within a predetermined range.

8. The IMD system of claim 1, wherein the control module is configured to control the low voltage circuit to generate the pacing pulse therapy during operation in the single lead mode.

9. The IMD system of claim 8, wherein the pacing pulse therapy includes one of a bradycardia pacing, anti-tachycardia pacing, or a post-shock pacing.

10. The IMD system of claim 1, wherein the control module is configured to control the high voltage circuit to generate a defibrillation shock therapy during operation in the single lead mode.

11. The IMD system of claim 1, wherein the control module is configured to control both the low voltage circuit and the high voltage circuit to generate the pacing pulse therapy and the defibrillation shock therapy during operation in the multi-lead mode.

12. The IMD system of claim 1, wherein the mode-selection module is programmable to switch between the single lead mode and the multi-lead mode.

13. The IMD system of claim 1, further comprising a conductive housing configured to function as a housing electrode, wherein the control module controls delivery of the pacing pulse therapy between the housing electrode and the pacing lead in the single lead mode.

14. The IMD system of claim 1, further comprising a conductive housing configured to function as a housing electrode, wherein the control module controls delivery of the defibrillation shock therapy between the housing electrode and the defibrillation lead in the single lead mode.

15. The IMD system of claim 1, further comprising a conductive housing configured to function as a housing electrode, wherein the control module controls delivery of one of the pacing pulse therapy or the defibrillation shock therapy between the housing electrode and the defibrillation lead in the multi-lead mode.

16. The IMD system of claim 1, wherein the pacing lead and the defibrillation lead each include at least one sensing electrode, and the control module controls delivery of at least one of the pacing pulse therapy and the defibrillation shock therapy as a function of the electrical activity sensed by the sensing electrode.

17. An implantable cardiac defibrillation (IMD) system comprising:
    a housing having a defibrillation lead port and a pacing lead port;
    a defibrillation lead configured to be connected to the defibrillation lead port;
    a pacing lead configured to be connected to the pacing lead port;
    a control module operable to control therapy delivery through the defibrillation lead and the pacing lead, wherein the control module selects between:
        a single lead mode under which the therapy is delivered through one of the pacing lead or the defibrillation lead; and
        a multi-lead mode that under which the therapy is delivered through both the pacing lead and the defibrillation lead, and wherein the control module receives a first connection signal indicative of a connection of the defibrillation lead to the defibrillation lead port and a second connection signal indicative of a connection of the pacing lead to the pacing lead port, and the control module selectively operates in:

the single lead mode triggered by receipt of the first connection signal or the second connection signal, or the multi-lead mode triggered by receipt of both the first connection signal and the second connection signal.

18. The IMD system of claim 17, further comprising:
a high voltage circuit coupled to the control and operable to generate a defibrillation shock therapy;
a low voltage circuit coupled to the control module and operable to generate a pacing pulse therapy; and
a mode-selection module configured to selectively activate at least one of the high voltage circuit and the low voltage circuit based on whether the control module is operating in the single lead mode or the multi-lead mode.

19. The IMD system of claim 17, wherein the control module is programmable to selectively switch between the single lead mode and the multi-lead mode.

20. A method performed by an implantable medical device (IMD) system, comprising:
performing a pacing lead recognition with a processor to determine whether a pacing lead is connected to a pacing lead port of the IMD;
performing a defibrillation lead recognition with a processor to determine whether a defibrillation lead is connected to a defibrillation lead port of the IMD;
generating a mode signal based on a result of the pacing lead recognition and a result of the defibrillation lead recognition;
selectively activating an operating mode of the IMD system in response to the mode signal, wherein a controller, in response to the mode signal, selects between:
a single defibrillation lead mode in which the IMD is configured to provide defibrillation shock therapy via the defibrillation lead;
a single pacing lead mode in which the IMD is configured to provide pacing pulse therapy via the pacing lead; and
a multi-lead mode in which the IMD is configured to provide pacing pulse therapy via the pacing lead and to provide defibrillation shock therapy via the defibrillation lead; and
generating at least one of a first connection signal in response to connection of the defibrillation lead to the defibrillation lead port, and a second connection signal in response to connection of the pacing lead to the pacing lead port, wherein the result of the defibrillation lead recognition indicates connection of the defibrillation lead triggered by receipt of the first connection signal, and the result of the pacing lead recognition indicates connection of the pacing lead triggered by receipt of the second connection signal.

21. The method of claim 20, further comprising receiving a sensed signal from the pacing lead to control the pacing pulse therapy delivery in in response to selective activation of the single lead mode.

22. The method of claim 20, further comprising receiving a sensed signal from the defibrillation lead to control at least one of the defibrillation shock therapy delivery and the pacing pulse therapy delivery in response to selective activation of the single lead mode.

23. The method of claim 20, further comprising receiving a sensed signal from at least one of the defibrillation lead and the pacing lead to control the pacing pulse therapy delivery and the defibrillation shock therapy delivery in response to selective activation of the multi-lead mode.

24. The method of claim 20, further comprising receiving implanting at least one of the pacing lead and the defibrillation lead within a substernal space of a patient.

25. The method of claim 20, further comprising selectively activating:
the high voltage circuit to generate the defibrillation shock therapy during the single defibrillation lead mode, or
the low voltage circuit to generate the pacing pulse therapy during the single pacing lead mode.

26. The method of claim 20, further comprising selectively activating at least one of the high voltage circuit to generate the defibrillation shock therapy and the low voltage circuit to generate the pacing pulse therapy during the multi-lead mode.

* * * * *